US012672784B2

(12) United States Patent
Mäkinen et al.

(10) Patent No.: US 12,672,784 B2
(45) Date of Patent: Jul. 7, 2026

(54) TECHNIQUES FOR MEASUREMENT PATH MULTIPLEXING FOR A WEARABLE DEVICE

(71) Applicant: Oura Health Oy, Oulu (FI)

(72) Inventors: Jukka Tapani Mäkinen, Oulu (FI);
Mika Petteri Kangas, Oulu (FI);
Jaakko Tapio Vartiainen, Oulu (FI);
Kirsi Marja Maansaari, Oulu (FI);
Olli Petteri Heikkinen, Oulu (FI)

(73) Assignee: Oura Health Oy, Oulu (FI)

( * ) Notice: Subject to any disclaimer, the term of this patent is extended or adjusted under 35 U.S.C. 154(b) by 764 days.

(21) Appl. No.: 18/155,484

(22) Filed: Jan. 17, 2023

(65) Prior Publication Data

US 2024/0237904 A1     Jul. 18, 2024

(51) Int. Cl.
*A61B 5/0205* (2006.01)
*A61B 5/00* (2006.01)
*A61B 5/024* (2006.01)
*A61B 5/1455* (2006.01)

(52) U.S. Cl.
CPC ........ *A61B 5/0205* (2013.01); *A61B 5/14552* (2013.01); *A61B 5/6802* (2013.01); *A61B 5/02405* (2013.01); *A61B 5/02427* (2013.01)

(58) Field of Classification Search
CPC ............ A61B 5/14552; A61B 5/02427; A61B 5/6826; A61B 5/6802; A61B 5/681
See application file for complete search history.

(56) References Cited

U.S. PATENT DOCUMENTS

| | | | | |
|---|---|---|---|---|
| 9,766,126 | B2 * | 9/2017 | Gulati | A61B 5/14552 |
| 10,918,289 | B1 * | 2/2021 | Wasson | A61B 5/14552 |
| 2006/0122520 | A1 * | 6/2006 | Banet | A61B 5/14552 |
| | | | | 600/323 |
| 2017/0000350 | A1 * | 1/2017 | Kwon | A61B 5/14552 |
| 2018/0132789 | A1 † | 5/2018 | Chen | |
| 2018/0296098 | A1 † | 10/2018 | Islam | |
| 2018/0333053 | A1 † | 11/2018 | Verkruijsse | |
| 2019/0360928 | A1 † | 11/2019 | Lasarov | |
| 2020/0315473 | A1 † | 10/2020 | Peterson | |
| 2024/0000328 | A1 † | 1/2024 | Kangas | |
| 2024/0122548 | A1 † | 4/2024 | Kangas | |

* cited by examiner
† cited by third party

*Primary Examiner* — Eric F Winakur
(74) *Attorney, Agent, or Firm* — ArentFox Schiff LLP

(57)     ABSTRACT

Methods, systems, and devices for measurement multiplexing for a wearable device are described. The method may include transmitting light using a light-emitting component of a wearable device via a set of transmission angles and receiving the light using a photodetector of the wearable device via a set of reception angles. Further, the method may include selecting a transmission angle from the set of transmission angles and a reception angle from the set of reception angles based on a comparison of a set of signal quality metrics associated with the set of transmission angles and the set of reception angles. The method may further include acquiring physiological data associated with the user using the transmission angle and the reception angle.

20 Claims, 9 Drawing Sheets

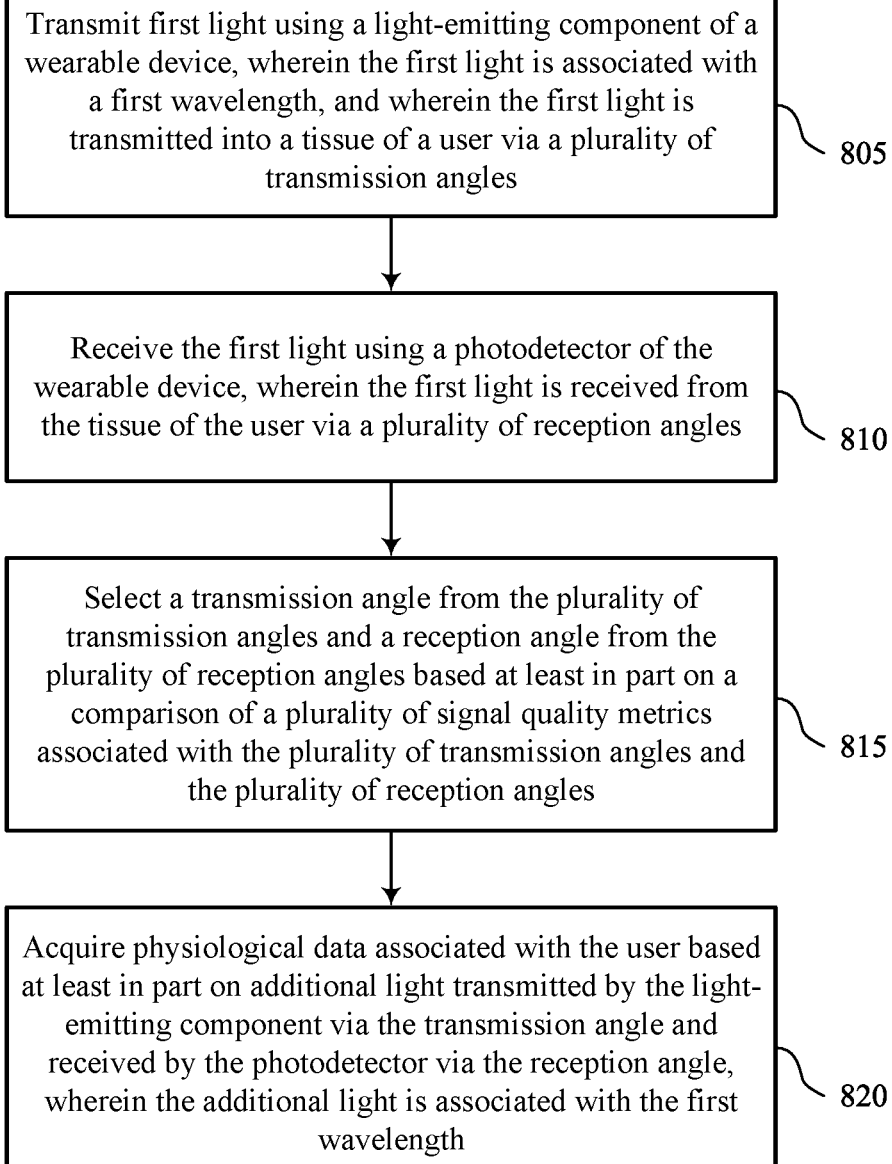

Transmit first light using a light-emitting component of a wearable device, wherein the first light is associated with a first wavelength, and wherein the first light is transmitted into a tissue of a user via a plurality of transmission angles

805

Receive the first light using a photodetector of the wearable device, wherein the first light is received from the tissue of the user via a plurality of reception angles

810

Select a transmission angle from the plurality of transmission angles and a reception angle from the plurality of reception angles based at least in part on a comparison of a plurality of signal quality metrics associated with the plurality of transmission angles and the plurality of reception angles

815

Acquire physiological data associated with the user based at least in part on additional light transmitted by the light-emitting component via the transmission angle and received by the photodetector via the reception angle, wherein the additional light is associated with the first wavelength

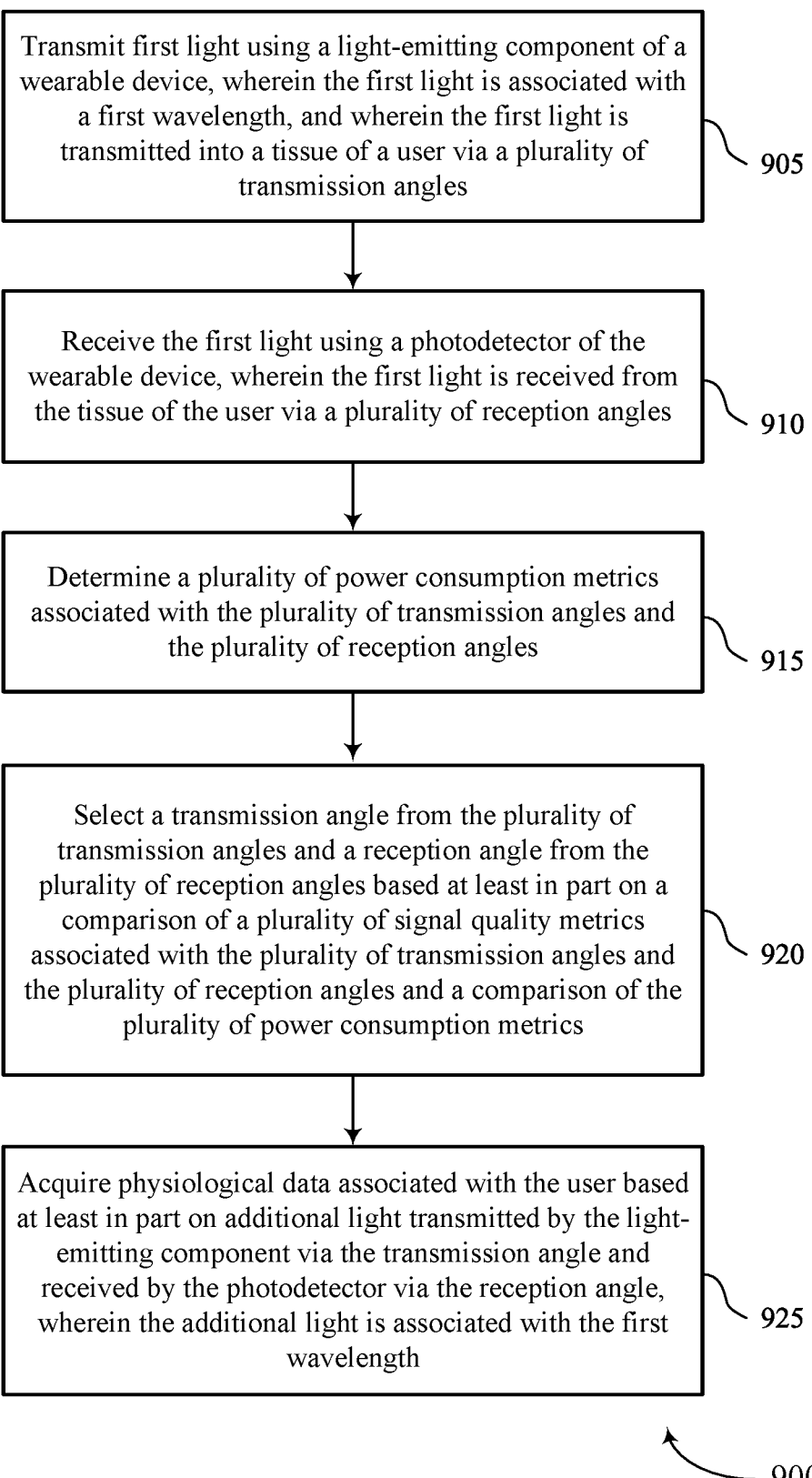

Transmit first light using a light-emitting component of a wearable device, wherein the first light is associated with a first wavelength, and wherein the first light is transmitted into a tissue of a user via a plurality of transmission angles ⟶ 905

Receive the first light using a photodetector of the wearable device, wherein the first light is received from the tissue of the user via a plurality of reception angles ⟶ 910

Determine a plurality of power consumption metrics associated with the plurality of transmission angles and the plurality of reception angles ⟶ 915

Select a transmission angle from the plurality of transmission angles and a reception angle from the plurality of reception angles based at least in part on a comparison of a plurality of signal quality metrics associated with the plurality of transmission angles and the plurality of reception angles and a comparison of the plurality of power consumption metrics ⟶ 920

Acquire physiological data associated with the user based at least in part on additional light transmitted by the light-emitting component via the transmission angle and received by the photodetector via the reception angle, wherein the additional light is associated with the first wavelength ⟶ 925

TECHNIQUES FOR MEASUREMENT PATH MULTIPLEXING FOR A WEARABLE DEVICE

FIELD OF TECHNOLOGY

The following relates to wearable devices and data processing, including techniques for measurement path multiplexing for a wearable device.

BACKGROUND

Some wearable devices may be configured to collect data, such as physiological data, from a user of the wearable device. To collect the data, the wearable device may analyze characteristics of light that is transmitted through the tissue of the user using optical components of the wearable device (e.g., optical transmitters and optical receivers). Further, the wearable device may utilize different wavelengths of light when collecting different physiological data because different wavelengths of light may penetrate the tissue at different depths. However, certain penetration depths may cause the light to interact with different physiological features within the user's tissue, such as bones and blood vessels, which may negatively impact the quality and reliability of some physiological measurements. For example, when collecting a blood oxygen saturation metric, it may beneficial for the light to not travel through the blood vessels because the blood oxygen saturation metric is based on absorption and the movement of the blood vessels may cause the light to reflect.

BRIEF DESCRIPTION OF THE DRAWINGS

FIGS. 8 and 9 illustrate flowcharts showing methods that support techniques for measurement path multiplexing for a wearable device in accordance with aspects of the present disclosure.

DETAILED DESCRIPTION

Figure 1:
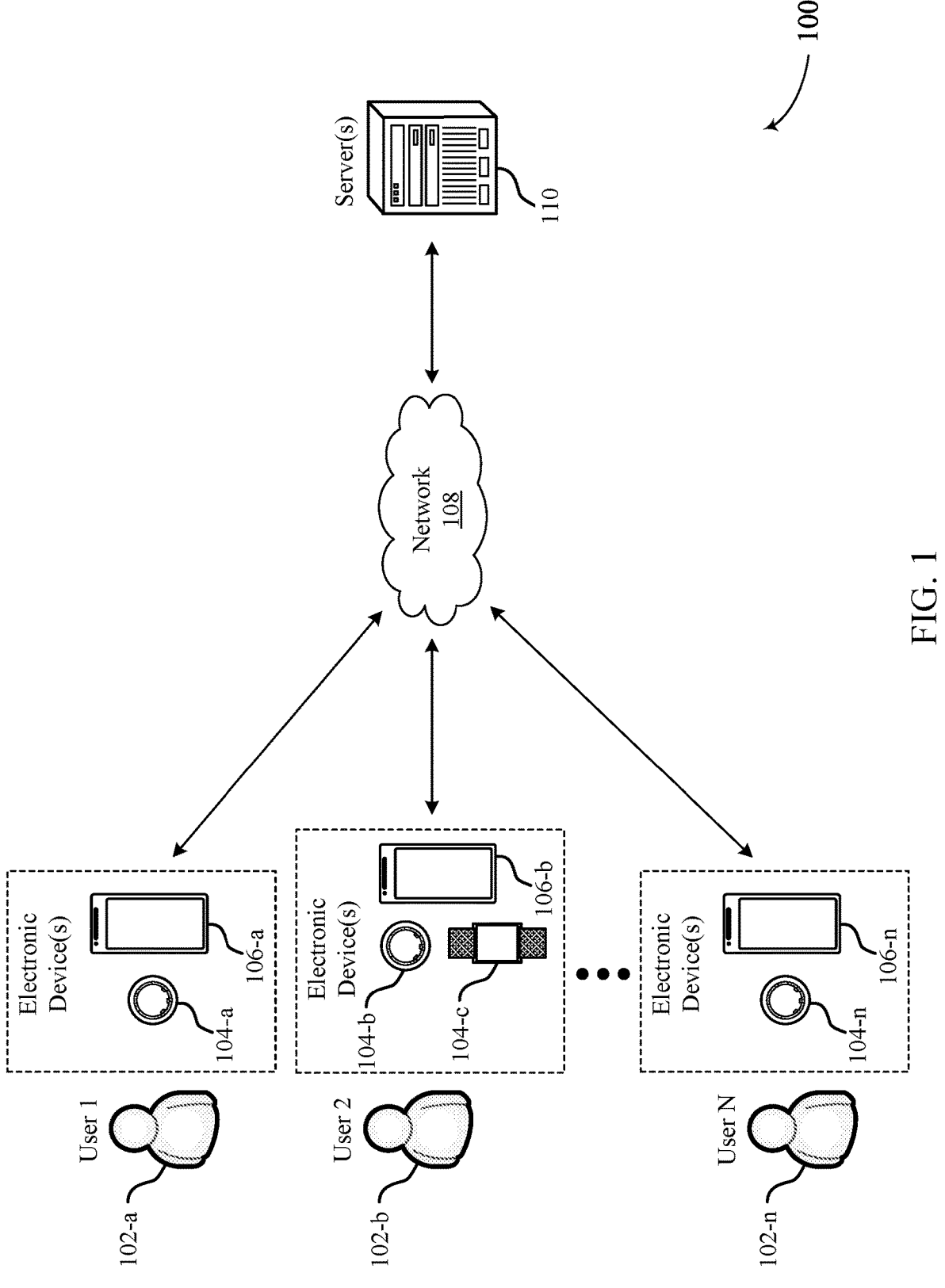
FIG. 1 illustrates an example of a system that supports techniques for measurement path multiplexing for a wearable device in accordance with aspects of the present disclosure.

A wearable device may be configured to collect physiological data from a user such that the user may monitor various aspects of their health. As an example, the wearable device may be configured to collect heart rate data, sleep data, or blood pressure data for the user. In order to collect the physiological data for the user, the wearable device may include a light-emitting component and a photodetector component. In some examples, the wearable device may be an example of a ring. In such examples, the light-emitting component and the photodetector component may be positioned along the inner-housing of the ring such that the light may travel through one or more layers of the user's finger.

In some examples, the light-emitting component may be capable of transmitting different wavelengths of light that is used to acquire physiological data. For example, the light-emitting component may be capable of transmitting red light, IR light, green light, or blue light. Different wavelengths of light may penetrate a different number of layers of the user's finger and may contribute to different physiological measurements. As such, different wavelengths may benefit from traveling along different optical paths through the user's finger (e.g., different penetration depths may be used for different physiological measurements). For example, red light and IR light may benefit from an optical path that goes through the pulsating vein of the finger.

In general, the penetration depth for a given optical path may be based on the wavelength of light that is used, as well as the distance between the light-emitting component and the photodetector. That is, IR light may result in different penetration depths depending on the distance between the light-emitting component and the photodetector. However, in most wearable devices, the locations of the light-emitting components and the photodetectors are fixed, meaning the distances between the respective components are also fixed. As such, in order to create different optical paths and/or penetration depths, the wearable device may activate different combinations of light-emitting components and photodetector components and/or may utilize different wavelengths of light. However, continually activating and deactivating different combinations of light-emitting components and photodetector components may increase power consumption at the wearable device. Moreover, including multiple combinations of light-emitting components and photodetector components in the wearable device may increase manufacturing costs of the wearable device. As such, conventional wearable devices may be relatively limited in the ability of the wearable devices to perform measurements with certain wavelengths of light at different penetration depths.

Accordingly, aspects of the current disclosure are directed to a wearable device having a capability to adjust an optical path for an optical package of the wearable device (e.g., a photodetector component and a corresponding light-emitting component). Different wavelengths of light or different physiological measurements may be associated with different penetration depths and therefore, may benefit from different optical paths. Thus, the aspects of the present disclosure may allow the wearable device to selectively adjust the optical path (e.g., penetration depth) for different wavelengths of light or different physiological measurements which may increase the accuracy of the physiological data. Further, compared to other methods (e.g., a method of including multiple optical packages within the wearable device to achieve multiple optical paths), the aspects as described herein may decrease power consumption at the wearable device as well as decrease manufacturing costs by enabling fewer light-emitting components and photodetectors to achieve a wider array of penetration depths used for physiological measurements.

In some examples, the wearable device may include a light emitting component and a photodetector component. The light emitting component may include an angular filter component that may allow the wearable device to selectively adjust a transmission angle of the light. Additionally, or alternatively, the photodetector component may include an angular filter component that may allow the wearable device to selectively adjust a reception angle of the light. Further, the wearable device may select a particular combination of a reception angle and a transmission angle for different situations (e.g., for different wavelengths of lights or different physiological measurements).

In particular, by enabling the wearable device to utilize different transmission and/or reception angles, techniques described herein may enable the wearable device to perform physiological measurements at varying penetration depths. By adjusting the transmission/reception angles, and therefore the penetration depth of light, techniques described herein may enable the wearable device to direct the light to hit or avoid certain physiological structures (e.g., bones, arteries, veins) in the user's tissue depending on the measurements being performed. As such, techniques described herein may enable the wearable device to test different combinations of transmission/reception angles (and therefore different penetrations depths) for respective wavelengths and/or types of physiological measurements to improve signal quality and/or reduce power consumption.

For example, the wearable device may transmit light using the light-emitting component via a set of transmission angles and receive the light using the photodetector component via a set of reception angles. The different combinations of transmission/reception angles may result in varying penetration depths into the tissue of the user, even in cases where the relative distance between the light-emitting component and the photodetector is fixed. Further, the wearable device may compare signal quality metrics associated with the set of transmission angles and the set of reception angles and select a transmission angle and a reception angle from the set based on the comparison. In some examples, the wearable device may select the transmission angle and the reception angle that is associated with a highest signal intensity, a lowest power consumption, or both. The wearable device may then acquire physiological data for the user using the selected transmission angle and the selected transmission angle.

Aspects of the disclosure are initially described in the context of systems supporting physiological data collection from users via wearable devices. Additional aspects are described in the context of a optical package. Aspects of the disclosure are further illustrated by and described with reference to apparatus diagrams, system diagrams, and flowcharts that relate to techniques for measurement path multiplexing for a wearable device.

FIG. 1 illustrates an example of a system 100 that supports techniques for measurement path multiplexing for a wearable device in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call display's), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state: 2) circadian rhythms: 3) non-endogenous daily rhythms shown to be imposed on top of circadian rhythms, as in work schedules: 4) weekly rhythms, or other artificial time periodicities exogenously imposed (e.g., in a hypothetical culture with 12 day "weeks," 12 day rhythms could be used): 5) multi-day ovarian rhythms in women and spermatogenesis rhythms in men: 6) lunar rhythms (relevant for individuals living with low or no artificial lights): and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for selectively adjusting an optical path between optical components of the wearable device 104. In some examples, the wearable device 104 may utilize light-emitting components (e.g., LEDs or laser diodes) and photodetectors to collect physiological data. When transmitting light via the light-emitting component, the wearable device 104 may selectively adjust the angle of transmission of the light. Further, in some examples, the wearable device 104 may selectively adjust the angle of reception of the light. Adjusting the transmission/reception angles may affect the penetration depth of a given wavelength of light into the tissue of the user. In order to selectively adjust the transmission angle or the reception angle, an angular filter component may be deposited on a surface of the light-emitting component or the photodetector. The angular filter component may be an example of a liquid crystal film, a prismatic structure, a micro-optical structure, or a dielectric angular filter. By selectively adjusting the transmission angle or the reception angle of the light, the wearable device 104 may effectively change the optical path along which the light travels or the penetration depth of the light.

In some examples, different wavelengths of light or different physiological measurements may benefit from different optical paths. That is, different penetration depths may be used to perform different physiological measurements. For example, heart rate measurements may be performed by directing light to a penetration depth that allows the light to hit or interact with blood vessels. Comparatively, pulsating blood vessels may be interpreted as noise when performing SpO2 measurements. As such, SpO2 measurements may be performed by directing light to a penetration depth which avoids blood vessels.

As such, the wearable device 104 may select a transmission angle and a reception angle that results in optical path that is beneficial for a particular wavelength of light or a physiological measurement. In one example, the light-emitting component of the wearable device 104 may transmit a first wavelength of light using a set of transmission angles and a photodetector may receive the first wavelength of light using a set of reception angles, resulting in multiple different angle combinations. In other words, the light-emitting component may "scan" through a set of transmission angles when transmitting light, and the photodetector may "scan" through a set of reception angels when receiving the light.

For each angle combination (e.g., for each transmission/reception angle pair), the wearable device 104 may determine a signal quality metric (e.g., signal strength or signal intensity), and the wearable device 104 may compare the signal quality metrics to one another. Additionally, or alternatively, the wearable device 104 may determine a power consumption metric for each angle combination, and may compare the power consumption metrics to one another. Additionally, or alternatively, the wearable device 104 may determine a penetration depth for each combination and compare the penetration depths to one another.

Using the comparison of one or more of the signal quality metrics, the power consumption metrics, and/or the penetration depths, the wearable device 104 may select a reception angle 330 and a transmission angle 335 for a particular wavelength of light or a physiological measurement. In one example, the wearable device 104 may select the reception angle 330 and the transmission angle that is associated with a highest signal quality metric (e.g., highest signal intensity), a lowest power consumption metric (e.g., least power drain on a battery of the wearable device 104), or both.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
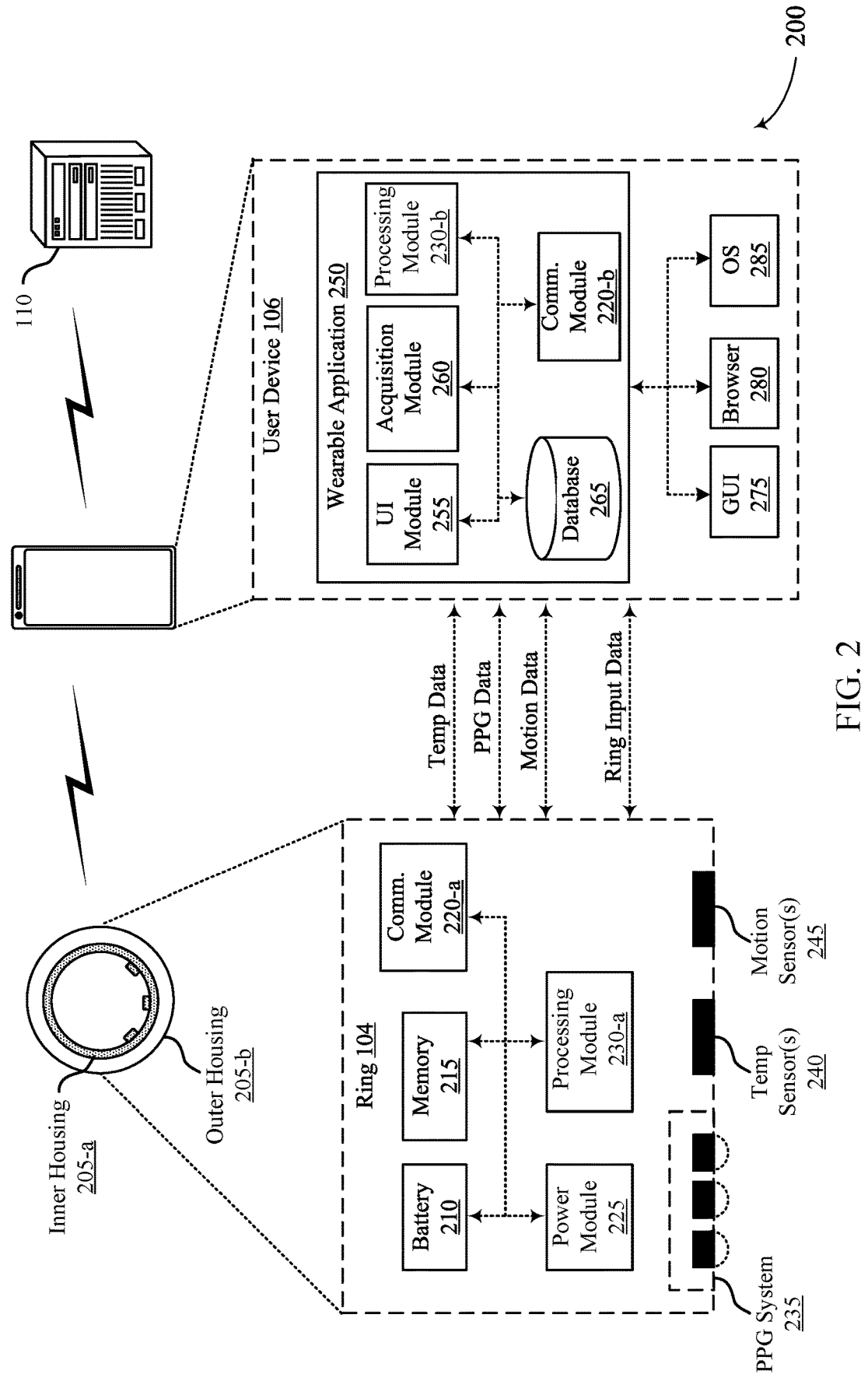
FIG. 2 illustrates an example of a system that supports techniques for measurement path multiplexing for a wearable device in accordance with aspects of the present disclosure.

FIG. 2 illustrates an example of a system 200 that supports techniques for measurement path multiplexing for a wearable device in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/ configuration updates. The user device 106 may process data. In some implementations, the user device 106 may transmit data to the server 110 for processing and/or storage.

The ring 104 may include a housing 205 that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, that may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-b. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/ battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-a may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-a may communicate with the memory 215. The memory 215 may include computer-readable instructions that, when executed by the processing module 230-a, cause the processing module 230-a to perform the various functions attributed to the processing module 230-a herein. In some implementations, the processing module 230-a (e.g., a microcontroller) may include additional features associated with other modules, such as communication functionality provided by the communication module 220-a (e.g., an integrated Bluetooth Low Energy transceiver) and/or additional onboard memory 215.

The communication module 220-a may include circuits that provide wireless and/or wired communication with the user device 106 (e.g., communication module 220-b of the user device 106). In some implementations, the communication modules 220-a, 220-b may include wireless communication circuits, such as Bluetooth circuits and/or Wi-Fi circuits. In some implementations, the communication modules 220-a, 220-b can include wired communication circuits, such as Universal Serial Bus (USB) communication circuits. Using the communication module 220-a, the ring 104 and the user device 106 may be configured to communicate with each other. The processing module 230-a of the ring may be configured to transmit/receive data to/from the user device 106 via the communication module 220-a. Example data may include, but is not limited to, motion data, temperature data, pulse waveforms, heart rate data, HRV data, PPG data, and status updates (e.g., charging status, battery charge level, and/or ring 104 configuration settings). The processing module 230-a of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240) module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep day's may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score)

may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for selectively adapting a transmission angle and a reception angle of optical components of a ring 104. In some examples, prior to obtaining physiological metrics for the user, the ring 104 may transmit one or more wavelengths of light via multiple transmission angles using an optical transmitter (e.g., LED, laser diode, etc.). Additionally, the ring 104 may receive the one or more wavelengths of light via multiple reception angles using an optical receiver (e.g., photodetector). For each combination of reception angle and transmission angle, the ring 104 may generate a signal (e.g., a PPG signal) that indicates a quality metric (e.g., signal intensity) of the light. The optical receiver may then pass the generated signals to the processing module 230-a. The processing module 230-a may compare the generated signals to one another and determine a best transmission angle and reception angle pair. The best transmission angle and reception angle pair may be associated with a generated signal that indicates a highest signal intensity value when compared to the other generated signals, a lowest power consumption metric, or both. The ring 104 may then utilize the selected reception angle and the selected transmission angle for future physiological measurements.

Figure 3:
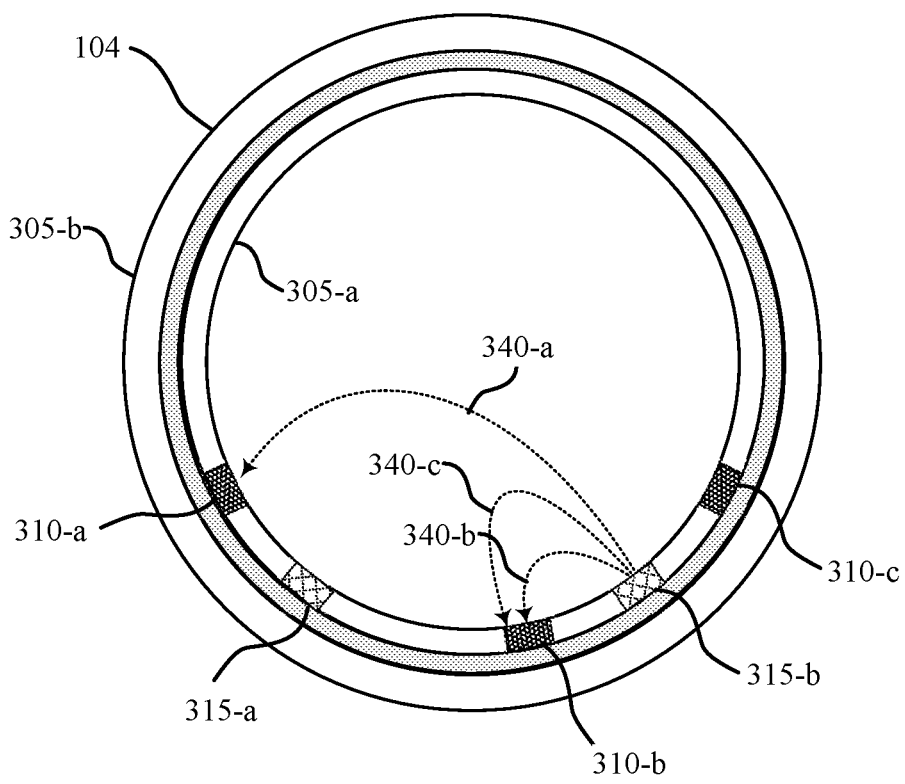
FIG. 3 illustrates an example of a system that supports techniques for measurement path multiplexing for a wearable device in accordance with aspects of the present disclosure.
Figure 3:
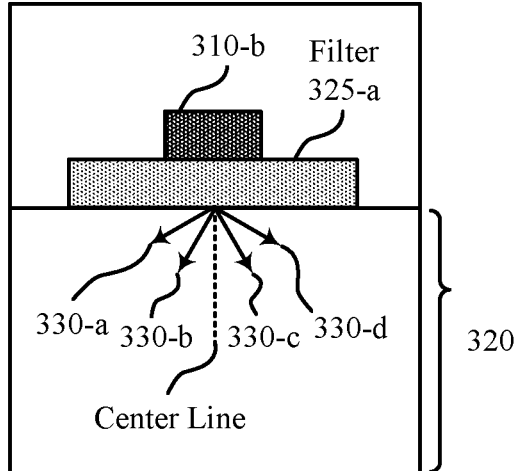
Figure 3:
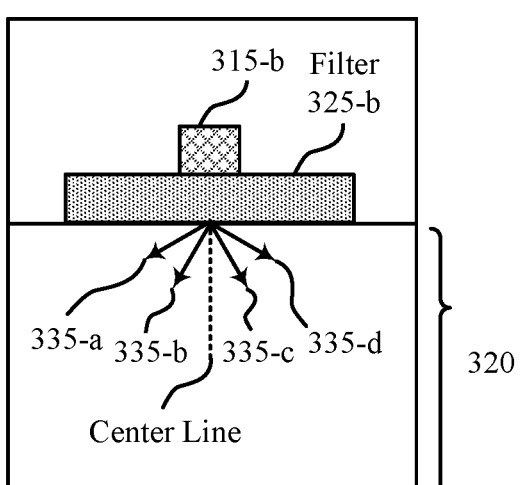

FIG. 3 illustrates an example of a system 300 that supports techniques for measurement path multiplexing for a wearable device in accordance with aspects of the present disclosure. In some examples, the system 300 may implement aspects of a system 100 and a system 200. For example, the system 300 may include a wearable device 104 which may be an example of a wearable device 104 or a ring 104 as described with reference to FIGS. 1 and 2. Further, as shown in FIG. 3, the wearable device 104 may include one or more optical components. For example, the wearable device 104 may include optical transmitters 315 and optical receivers 310. The optical transmitters 315 and the optical receivers 310 may be examples of optical transmitters and optical receivers of the PPG system 235 as described with reference to FIG. 2.

As described with reference to FIG. 2, a wearable device 104 may utilize optical components (e.g., optical transmitters 315 and optical receivers 310) to obtain physiological measurements of the user. An optical transmitter 315 of the wearable device 104 may be configured to emit light and an optical receiver 310 may be configured to receive the light emitted from the optical transmitter 315. Further, the optical transmitter 315 may be capable of emitting light of different wavelengths and the optical receiver 310 may be capable of receiving light of different wavelengths from the optical transmitter 315. For example, the optical transmitter 315 may transmit red light (e.g., light with a wavelength of approximately 660 nm), green light (e.g., light with a wavelength of approximately 530 nm), and IR light (e.g., light with a wavelength of approximately 530 nm). The optical transmitters 315 may include any light-emitting component including, but not limited to, LEDs, lasers, and the like.

The optical transmitter 315 may emit the light and the light may travel along a optical path 340 to the optical receiver 310. For example, as shown in FIG. 3, the optical transmitter 315-*b* may emit light and the light may travel along optical path 340-*a* to the optical receiver 310-*a*. However, it may be beneficial for lights of different wavelengths to travel along different signal paths 340, for example, to hit or avoid certain physiological features in the user's tissue, such as bones or blood vessels. As described in FIG. 2, the wearable device 104 may utilize different wavelengths of light to obtain different physiological measurements of the user. For example, red light and IR light may penetrate the epidermis, the dermis, and the hypodermis of the user's finger and can therefore be utilized to obtain physiological measurements such as a blood oxygen saturation of the user. Alternatively, green light may penetrate the epidermis and the dermis of the user's finger and can therefore be utilized to obtain physiological measurements such as top layer skin perfusion. Thus, it may be beneficial for the red light and the IR light to travel along a optical path 340 that is through the epidermis, the dermis, and the hypodermis and it may be beneficial for the green light to travel along a optical path 340 through the epidermis and the dermis (e.g., a different optical path 340) such that the green light does not interfere with deeper signal paths (e.g., red light or IR light).

To achieve different signals path 340 for different wavelengths of light, the wearable device 104 may select and activate different optical packages (e.g., different combinations of optical transmitters 315 and optical receivers 310). For example, the wearable device 104 may select the optical transmitter 315-*b* and the optical receiver 310-*a* when transmitting red light and IR light such that the red light and the IR light travel along optical path 340-*a* and the wearable device 104 may select the optical transmitter 315-*b* and the optical receiver 310-*b* when transmitting green light such that the green light travels along optical path 340-*b*. However, repeatedly activating and deactivating different optical components may increase power consumption at the wearable device 104. Further, including multiple different optical packages in the wearable device 104 may occupy an amount of space that could be potentially used for other crucial components of the wearable device 104 (e.g., temperature sensors or motion sensors).

Furthermore, the penetration depth for a given optical path 340 may be based on the wavelength of light that is used, as well as the distance between the respective optical transmitter 315 and optical receiver 310 being used. That is, IR light exchanged between the optical transmitter 315-*b* and the optical receiver 310-*b* may result in a different penetration depth as compared to IR light exchanged between the optical transmitter 315-*b* and the optical receiver 310-*a*. However, in most wearable devices, the locations of the optical transmitters 315 and optical receivers 310 are fixed, meaning the distances between the respective components (and corresponding penetrations depths of various wavelengths) are also fixed.

In larger wearable devices 104, the optical transmitters 315 and optical receivers 310 may be positioned in such a manner as to enable optimal penetration depths for light of certain wavelengths exchanged between the devices. For example, in the context of a wearable watch device, a light-emitting component and a photodetector may be arranged some distance away from one another such that the distance allows for green light exchanged between the devices to achieve an optimal penetration depth for certain measurements. However, smaller wearable devices (e.g., wearable ring devices 104) may be more limited in the geometrical arrangement of sensors, and may not be able to position sensors away from one another by certain distances that result in optimal penetration depths. As such, the physical/geometric constraints of some conventional wearable devices may limit the flexibility of the wearable devices to achieve certain penetration depths, and therefore limit the quality of acquired physiological data.

As described herein, a wearable device 104 may utilize optical filters to direct lights of different wavelengths along different signal paths 340. In some examples, a filter 325 (e.g., angular filter component) may be deposited on one or more optical transmitters 315 or one or more optical receivers 310 of the wearable device 104. In some examples, the filter 325 may be deposited on an exposed surface of the optical transmitter 315 or the optical receiver 310. The exposed surface may be described as a surface of the optical transmitter 315 or the optical receiver 310 from which light is transmitted or received, respectively. Further, the exposed surface may be a the surface of the optical transmitter 315 or the optical receiver 310 that is closest to (e.g., facing, proximate to) the user's finger. The filter 325 may be an example of an angular filter, a prismatic structure, a microoptical structure (e.g., diffractive optical components, Fresnel lenses, microprisms, etc.), or a pixeled structure.

In some examples, the wearable device 104 may select the optical transmitter 315-*b* and the optical receiver 310-*b* (e.g., to perform physiological measurements). In such examples, a filter 325-*a* may be deposited on one or both of the optical transmitter 315-*b* or the optical receiver 310-*b*. For example, as shown in FIG. 3, the filter 325-*a* may be deposited on the surface of the optical receiver 310-*b* such that the filter 325-*a* is positioned between the optical receiver 310-*b* and the epidermis 320 (e.g., epidermis of the user's finger). Further, as shown in FIG. 3, the filter 325-*b* may be deposited on the surface of the optical transmitter 315-*b* such that the filter 325-*b* is positioned between the optical transmitter 315-*b* and the epidermis 320 (e.g., epidermis of the user's finger). Although not shown in FIG. 3, it is understood that one or more other optical transmitters 315 (e.g., optical transmitter 315-*a*) and one or more other optical receivers 310 (e.g., optical receiver 310-*a* and optical receiver 310-*b*) of the wearable device 104 may have filters 325 similar to that of optical receiver 310-*b* and optical transmitter 315-*b*. That is, the methods as described herein are not limited to one optical transmitter 315 and one optical receiver 310.

In some examples, the filter 325 may be an example of a pixeled structure. In such example, one or more optical receivers 310 may be an example of a pixelated sensor that has a pixelated angular filter component on the top of it. Each pixel of the optical receiver 310 may be equal distance away from a respective optical transmitter 315, but each pixel may receive light in a different direction. In some examples, the wearable device 104 may activate all of the pixels of the optical receiver 310 during a same duration such that the pixels may act as a combined array which may result in a stronger signal (e.g., when compared to activating a single pixel). Further, one or more of the optical transmitters 315 may be example of a micro-optical structure capable of operating as a micro-optical array. Combining the pixelated sensor with the micro-optical array may allow for light field imagining which may allow the wearable device 104 to adjust the spatial separation and the angular domain of transmitted light.

The filters 325 may define a field of view (e.g., a field of view that is less than or equal to 180 degrees) for the optical receiver 310-*b* and the optical transmitter 315-*b*. For example, the filter 325-*a* may allow the optical receiver 310-*b* to receive light from the optical transmitter 315-*b* via a wide range of reception angles 330, including a reception angle 330-*a*, a reception angle 330-*b*, a reception angle 330-*c*, or a reception angle 330-*d*. A reception angle 330 may represent a singular angle value or a range of angle values. For example, a reception angle 330-*a* may represent an angle value of –60 or an angle range of –45 degrees to –90 degrees: a reception angle 330-*b* may represent an angle value of –30 or an angle range of 0 degrees to –45 degrees: a reception angle 330-*c* may represent an angle value of 30 or an angle range of 0 degrees to 45 degrees: and a reception angle 330-*d* may represent an angle value of 60 or an angle range of 45 degrees to 60 degrees. The reception angles 330-*a*, 330-*b* may be facing away from the optical transmitter 315-*b*, whereas the reception angle 330-*c*, 330-*d* may be facing towards the optical transmitter 315-*b*. Each reception angle 330 may be measured with respect to the center line. Further, the reception angles 330 are merely for illustrative purposes and it is understood that other angles (e.g., different from the reception angles 330) are possible.

Additionally, or alternatively, the filter 325-*b* may allow the optical transmitter 315-*b* to transmit according to a wide range of transmission angles 335, including a transmission angle 335-*a*, a transmission angle 335-*b*, a transmission angle 335-*c*, and a transmission angle 335-*d*. In some examples, the transmission angles 335 may be similar to the angles or angle ranges described with reference to the reception angles 330. The transmission angles 335-*a*, 335-*b* may be facing towards the optical receiver 310-*b*, whereas the transmission angles 335-*c*, 335-*d* may be facing away from the optical receiver 310-*b*.

The addition of the filter(s) 325 may allow the wearable device 104 to manipulate the optical path 340 (and therefore the penetration depth) that the light travels when being transmitted from the optical transmitter 315-*b* and received at the optical receiver 310-*b*. For example, without the filter(s) 325, the light may travel along the optical path 340-*b*. Comparatively, with the filter(s) 325, the light may follow a different optical path 340 that may be associated with a different penetration depth. For example, if the filter 325-*b* causes the light to be transmitted at the transmission angle 335-*d* at the optical transmitter 315-*b* and the filter 325-*a* causes the field of view of the optical receiver 310-*b* to be reception angle 330-*a*, the resulting optical path 340 may be optical path 340-*c*. The optical path 340-*c* may be different from the optical path 340-*b* in that the optical path 340-*c* is longer than the optical path 340-*b* and may potentially travel through more layers of the user's finger than the optical path 340-*b*. Thus, utilizing the filter(s) 325 may allow the wearable device 104 to achieve a longer optical path 340 (e.g., deeper penetration depth) with a more compact optical package.

With such a design, the wearable device 104 may potentially utilize the optical transmitter 315-*b* and the optical receiver 310-*b* to transmit red light and IR light as opposed to the optical transmitter 315-*b* and the optical receiver

310-*a*. The distance between the optical transmitter 315-*b* and the optical receiver 310-*b* relative to the inner surface of the wearable device 104 is less than the distance between the optical transmitter 315-*b* and the optical receiver 310-*a*. Thus, the optical transmitter 315-*b* and the optical receiver 310-*b* is a more compact optical package than the optical transmitter 315-*b* and the optical receiver 310-*a*

Further, in some examples, the filter(s) 325 may be adjustable. For example, the filter(s) 325 may be a liquid crystal film. Properties of the liquid crystal film (e.g., physical characteristics or crystalline structure) may change when an electrical stimulus is applied. For example, a filter 325 may allow light to be transmitted or received at a first angle (e.g., a reception angle 330 or a transmission angle 335) when a first voltage is applied to the filter 325 and the filter 325 may allow the light to be transmitted or received at a second angle when a second voltage is applied to the filter 325. The wearable device 104 may select a combination of a reception angle 330 and a transmission angle 335 from multiple combinations that is most applicable to a situation. For example, the wearable device 104 may select the reception angle 330-*d* and the transmission angle 335-*a* when utilizing green light, and select the reception angle 330-*a* and the transmission angle 335-*d* when utilizing IR light or red light.

Further, the wearable device 104 may perform a procedure in order to determine an optimal combination of a transmission angle and a reception angle for a particular situation. The procedure may include the wearable device 104 sweeping through multiple reception angles 330 and/or transmission angles 335 and selecting a best reception angle 330 and transmission angle 335 combination for obtaining future physiological measurements. In such examples, the wearable device 104 may adjust the filter 325-*b* such that the optical transmitter 315-*b* transmits light via the transmission angles 335. The optical transmitter 315-*b* may sweep through the respective transmission angles 335-*a*, 335-*b*, 335-*c*, 335-*d* sequentially or in any other order. Further, the optical transmitter 315-*b* may perform more than one sweep and each sweep may correspond to a different order of transmission angles 335. In some examples, the optical transmitter 315-*b* may perform the sweep for each light wavelength (e.g., green light, red light, and IR light). In some examples, the optical transmitter 315-*b* may be an example of a laser and the wearable device 104 may scan the laser through the angles 335 (e.g., using a prismatic structure as the filter 325-*b*).

Additionally, or alternatively, wearable device 104 may adjust the filter 325-*a* such that the optical receiver 310-*b* has a field of view corresponding to the angle 330-*a*, the angle 330-*b*, the angle 330-*c*, and the angle 330-*d* for receiving the light from the wearable device 104. In other words, the optical receiver 310-*b* may sweep through the respective reception angles 330-*a*, 330-*b*, 330-*c*, and 330-*d* sequentially or in any other order. Further, the optical receiver 310-*b* may perform more than one sweep and each sweep may correspond to a different order of angles 330. In some cases, the sweep across the transmission angles 335 at the optical transmitter 315-*b* and the sweep across the reception angles 330 at the optical receiver 310-*b* may be performed at the same or different times.

For each pair of transmission angles 335 and reception angles 330, the wearable device 104 may determine a signal quality metric. In one example, the signal quality metrics may include a signal strength or signal intensity of the light received at the optical receiver 310-*b*. For example, the wearable device 104 may determine a signal quality metric for a first pair of angles (e.g., the reception angle 330-a and the transmission angle 335-d), a second pair of angles (e.g., the reception angle 330-b and the transmission angle 335-c), a third pair of angles (e.g., the reception angle 330-c and the transmission angle 335-b), and a fourth pair of angles (e.g., the reception angle 330-d and the transmission angle 335-a). The wearable device 104 may compare the signal quality metrics and determine which pair of angle is associated with a best signal quality metric (e.g., a highest signal strength).

Further, in some examples, the wearable device may additionally determine a power consumption metric for each pair of angles, the power consumption metrics may indicate the amount of power used to transmit the light using the corresponding angle pair. The wearable device 104 may take into account the power consumption metrics when selecting the optical pair of angles. For example, if the second pair of angles has a slightly lower signal quality metric than the first pair of angles, but has a lower power consumption metric than the first pair of angles, the wearable device 104 may select the first pair of angles.

Further, the wearable device 104 may take into account the physiological measurement being performed when selecting the pair of transmission and reception angles. For example, the wearable device 104 may measure a blood oxygen saturation level of the user using red light and IR light. In such examples, the wearable device 104 may select a pair of angles that achieves an acceptable penetration depth for blood oxygen saturation level measurements. For example, the wearable device 104 may select from pairs of angles that include one of the reception angle 330-a and the reception angle 330-b and one of the transmission angle 335-c and the transmission angle 335-d. Such pairs of angles may result in an optical path 340 that passes through the pulsating vein of the user's finger.

In another example, the wearable device 104 may measure a skin top layer perfusion of the user using green light. In such examples, the wearable device 104 may select a pair of angles that achieve an acceptable penetration depth for skin top layer perfusion and results in a optical path 340 that does not interfere with deeper signal paths 340 (e.g., the signal path for measuring blood oxygen concentration levels). For example, the wearable device 104 may select from pairs of angles that include one of the reception angle 330-c and the reception angle 330-d and one of the transmission angle 335-a, and the transmission angle 335-b. Such pairs of angles may result in an optical path 340 that does not pass through the pulsating vein of the user's finger. Thus, it may be possible for the wearable device 104 to isolate different physiological phenomena from each other and cancel their noise components.

In addition to selecting the most optimal pair of angles, the wearable device 104 may also select the best optical package (e.g., select which optical transmitter 315 and/or which optical receiver 310 will be used). In some examples, the wearable device 104 may include multiple optical packages. For example, as shown in FIG. 3, the wearable device 104 may include at least first optical package (e.g., the optical transmitter 315-b and the optical receiver 310-b), a second optical package (e.g., the optical transmitter 315-b and the optical receiver 310-c), a third optical package (e.g., the optical transmitter 315-b and the optical receiver 310-c), and a fourth package (e.g., the optical transmitter 315-a and the optical receiver 310-a). A distance between the optical receiver 310 and the optical transmitter 315 for each optical package may be the same or different. Further, at least one component of an optical package may be at a different location along the inner surface of the wearable device 104 than a different optical package. Thus, the signal paths 340 associated with each of the packages may pass through different parts of the user finger. Additionally, in some examples, the optical transmitters 315 and the optical receivers 310 included in the optical packages of the wearable device 104 may have a filter disposed on top of their exposed surfaces (e.g., similar to the optical transmitter 315-b and the optical receiver 310-b).

To determine which optical package to activate or select, the wearable device 104 may perform a sweep (e.g., sweep across respective transmission angles 335 and reception angles 330) for each optical package. For example, for each optical package, the wearable device 104 may transmit light and receive light using a set of transmission angles 335 and a set of reception angles 330, respectively. After performing the sweep, the wearable device 104 may select the best optical package. As one example, the wearable device 104 may select the optical package that is associated with a highest combined signal quality metric (e.g., summation of all of the signal strength values of the angle pairs for that optical package). Upon selecting the optical package, the wearable device 104 may select an angle pair for the selected optical package (e.g., using the same sweeping operation that was used to determine the optical package or a different sweeping operation).

In this regard, aspects of the present disclosure may enable the wearable device 104 to select not only which optical transmitter 315/optical receiver 310 pairs will be used for collecting physiological data, but also which transmission angle 335/reception angle 330 pairs will be used. As such, techniques described herein may enable improved flexibility for performing physiological data measurements by enabling the wearable device 104 to select sensors and angle pairs that result in improved data quality and/or reduced power consumption.

In some examples, the wearable ring 104 may rotate around the user's finger. For example, the wearable ring 104 may rotate counter-clockwise such that the third optical package is situated along the top portion of the wearable device 104 and on the topside of the user's finger. The wearable device 104 may perform more accurate physiological measurement when the optical package of the wearable device 104 is situated along the bottom portion of the wearable device 104 and on the underside of the user's finger. As such, the wearable device 104 may determine (e.g., from the sweeping) that the third optical package is associated with a lower signal quality metric than the fourth optical package and as a result may select the fourth optical package. Moreover, techniques described herein may enable more robust data measurement even in cases where the wearable device 104 becomes rotated. For example, if the wearable device 104 becomes rotated, the wearable device 104 may re-select an optical package and/or transmission/reception angle pair that results in sufficient quality, even when the respective optical transmitters 315 and/or optical receivers 310 are rotated away from the "ideal" position on the user's finger for data measurement.

Upon selecting the transmission angle 335 and reception angle 330 pair, the wearable device may obtain physiological measurements using the selected transmission angle and reception angle pair. For example, using the optical transmitter 315-b, the wearable device 104 may transmit the light via the selected angle 335 and using the optical receiver 310-b, the wearable device 104 may receive the light via the selected angle 330. The wearable device 104 may compare the transmitted light and received light and determine a physiological metric based on the comparison.

Figure 4:
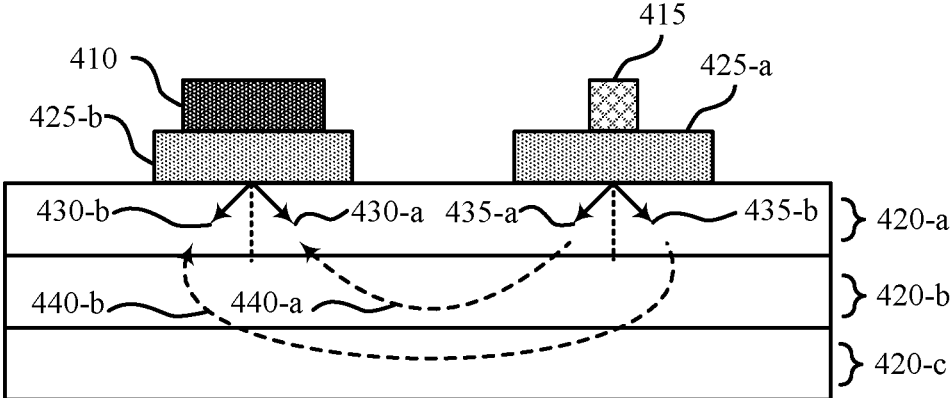
FIG. 4 illustrates an example of an optical package that supports techniques for measurement path multiplexing for a wearable device in accordance with aspects of the present disclosure.

FIG. 4 illustrates an example of an optical package 400 that supports techniques for measurement path multiplexing for a wearable device in accordance with aspects of the present disclosure. In some examples, the optical package 400 may implement aspects of a system 100, a system 200, and a system 300. For example, the optical package 400 may include optical transmitter 415 and an optical receiver 410 which may be an example of an optical transmitter 315 and an optical receiver 310 as described with reference to FIG. 3.

In some examples, a wearable device (e.g., a ring) may include an optical transmitter 415 and an optical receiver 410. The optical transmitter 415 may be disposed within a surface (e.g., inner surface) of the wearable device at a first position and the optical receiver 410 may be disposed within the surface (e.g., inner surface) of the wearable device at a second position that is a distance away from the optical transmitter 415. As described with reference to FIG. 3, the wearable device may adjust a field of view of one or both of the optical transmitter 415 and the optical receiver 410. In some examples, the wearable device may implement a filter (e.g., angular filter component) in combination with the optical receiver 410 or the optical transmitter 415. For example, as shown in FIG. 4, a filter 425-*b* (e.g., a first angular filter component) may be deposited on a surface of the optical receiver 410. Additionally, or alternatively, a filter 425-*a* (e.g., a second angular filter component) may be deposited on a surface of the optical transmitter 415. The filters 425 may be situated between their respective optical components (e.g., optical transmitter 415 or the optical receiver 410) and the user's finger.

The filter 425-*a* may allow the optical transmitter to transmit light (e.g., or a laser) via a transmission angle 435-*b* or a transmission angle 435-*a*. The transmission angle 435-*a* may face towards the optical receiver 410 and the transmission angle 435-*b* may face away from the optical receiver 410. Further, the filter 425-*b* may allow the optical receiver 410 to receive the light (e.g., or the laser) via a reception angle 430-*a* or a reception angle 430-*b*. The reception angle 430-*a* may face towards the optical transmitter 415 and the reception angle 430-*b* may face away from the optical transmitter 415. As described with reference to FIG. 3, the wearable device may select a transmission direction (e.g., a transmission angle 435) and a reception direction (e.g., direction 430) to utilize for a future physiological measurement of the user. In order for the wearable device to determine the transmission angle 435 and the reception angle 430, the optical transmitter 415 may transmit light via a set of transmission angles 435 that includes at least the transmission angle 435-*a* and the transmission angle 435-*b*. Further, the optical receiver 410 may receive the light via a set of reception angles 430 that includes at least the reception angle 430-*a* and the reception angle 430-*b*.

The wearable device may analyze the received light and select a transmission angle from the set of transmission angles 435 and a reception angle from the set of reception angles 430. In some examples, the wearable device may utilize one or more parameters to select the transmission angle and the reception angle. One parameter may be a signal quality of the received light. In such examples, the wearable device may select a transmission angle 435 and a reception angle 430 that results in a highest signal quality (e.g., light intensity) of the received light. Additionally, or alternatively, the wearable device may select a transmission angle and a reception angle based on the future physiological measurement to be obtained using the selected transmission angle and the selected reception angle or the wavelength of light used to obtain the physiological measurement.

As shown in FIG. 4, light transmitted using the transmission angle 435-*b* and received using the reception angle 430-*b* may follow an optical path 440-*b*. The optical path 440-*b* may penetrate layer 420-*a*, layer 420-*b* and layer 420-*c* of the user's finger. The layer 420-*a* may be an example of the epidermis of the user's finger, the layer 420-*b* may be an example of the dermis of the user's finger, and the layer 420-*c* may be an example of the hypodermis of the user's finger. Alternatively, light transmitted using the transmission angle 435-*a* and received using the reception angle 430-*a* may follow an optical path 440-*a*. The optical path 440-*a* may penetrate the layer 420-*a* and 420-*b*. As such, the penetration depth of the transmission angle 435-*b* and the reception angle 430-*b* is deeper than the penetration depth of the transmission angle 435-*a*.

Different wavelengths of light may penetrate the skin at different depth. For example, red light and IR light may penetrate the layer 420-*a*, the layer 420-*b*, and the layer 420-*c*, blue light may penetrate the layer 420-*a*, and green light may penetrate the layer 420-*a*. As such, the wearable device may utilize different wavelengths of light to determine different physiological measurements of the user. For example, the wearable device may utilize the red light and the IR light to determine a blood oxygen saturation metric of the user and the wearable device may utilize blue light or green light to determine a skin top layer perfusion of the user. Thus, when transmitting or receiving red light and IR light, the wearable device may select a transmission angle 435 and a reception angle 430 that penetrates the layer 420-*a*, the layer 420-*b*, and the layer 420-*c* (e.g., direction 435-*b* and direction 430-*b*).

Further, although green light and blue light do not penetrate as deep as IR light and red light, transmitting the green light or the blue along the same optical path 440 as the red light and the IR light may potentially affect the physiological measurements made using the red light and the IR light. As such, when transmitting and receiving the green light or the blue light the wearable device may select a transmission direction and a reception direction that penetrates only the layer 420-*a* and the layer 420-*b* (e.g., transmission angle 435-*a* and reception angle 430-*a*). This makes it possible for the wearable device to isolate different physiological phenomena from each other and cancel their noise components.

Figure 5:
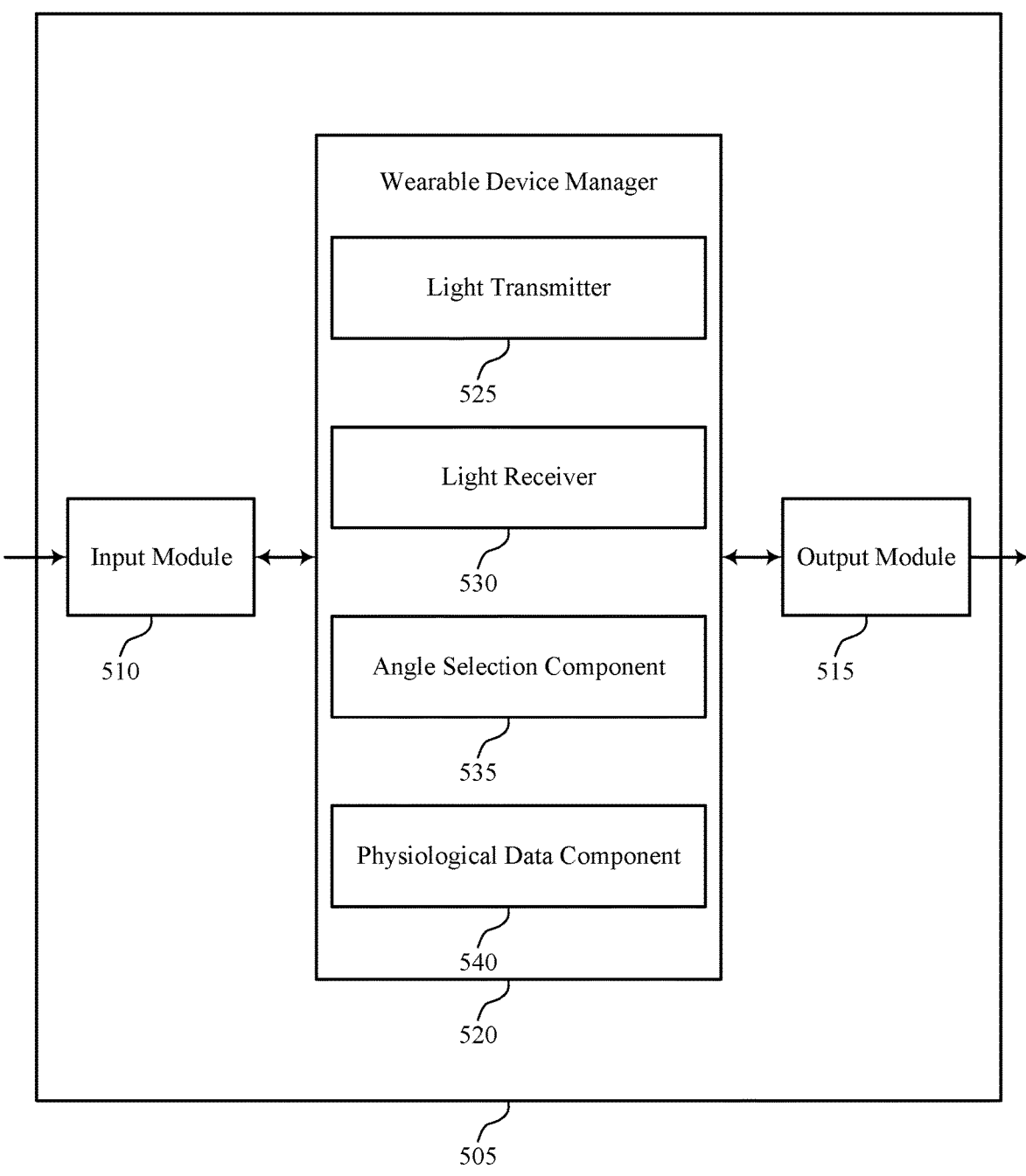
FIG. 5 illustrates a block diagram of an apparatus that supports techniques for measurement path multiplexing for a wearable device in accordance with aspects of the present disclosure.

FIG. 5 illustrates a block diagram 500 of a device 505 that supports techniques for measurement path multiplexing for a wearable device in accordance with aspects of the present disclosure. The device 505 may include an input module 510, an output module 515, and a wearable device manager 520. The device 505 may also include a processor. Each of these components may be in communication with one another (e.g., via one or more buses).

For example, the wearable device manager 520 may include a light transmitter 525, a light receiver 530, an angle selection component 535, a physiological data component 540, or any combination thereof. In some examples, the wearable device manager 520, or various components thereof, may be configured to perform various operations (e.g., receiving, monitoring, transmitting) using or otherwise in cooperation with the input module 510, the output module 515, or both. For example, the wearable device manager 520 may receive information from the input module 510, send information to the output module 515, or be integrated in combination with the input module 510, the output module 515, or both to receive information, transmit information, or perform various other operations as described herein.

The light transmitter 525 may be configured as or otherwise support a means for transmitting first light using a light-emitting component of a wearable device, wherein the first light is associated with a first wavelength, and wherein the first light is transmitted into a tissue of a user via a plurality of transmission angles. The light receiver 530 may be configured as or otherwise support a means for receiving the first light using a photodetector of the wearable device, wherein the first light is received from the tissue of the user via a plurality of reception angles. The angle selection component 535 may be configured as or otherwise support a means for selecting a transmission angle from the plurality of transmission angles and a reception angle from the plurality of reception angles based at least in part on a comparison of a plurality of signal quality metrics associated with the plurality of transmission angles and the plurality of reception angles. The physiological data component 540 may be configured as or otherwise support a means for acquiring physiological data associated with the user based at least in part on additional light transmitted by the light-emitting component via the transmission angle and received by the photodetector via the reception angle, wherein the additional light is associated with the first wavelength.

Figure 6:
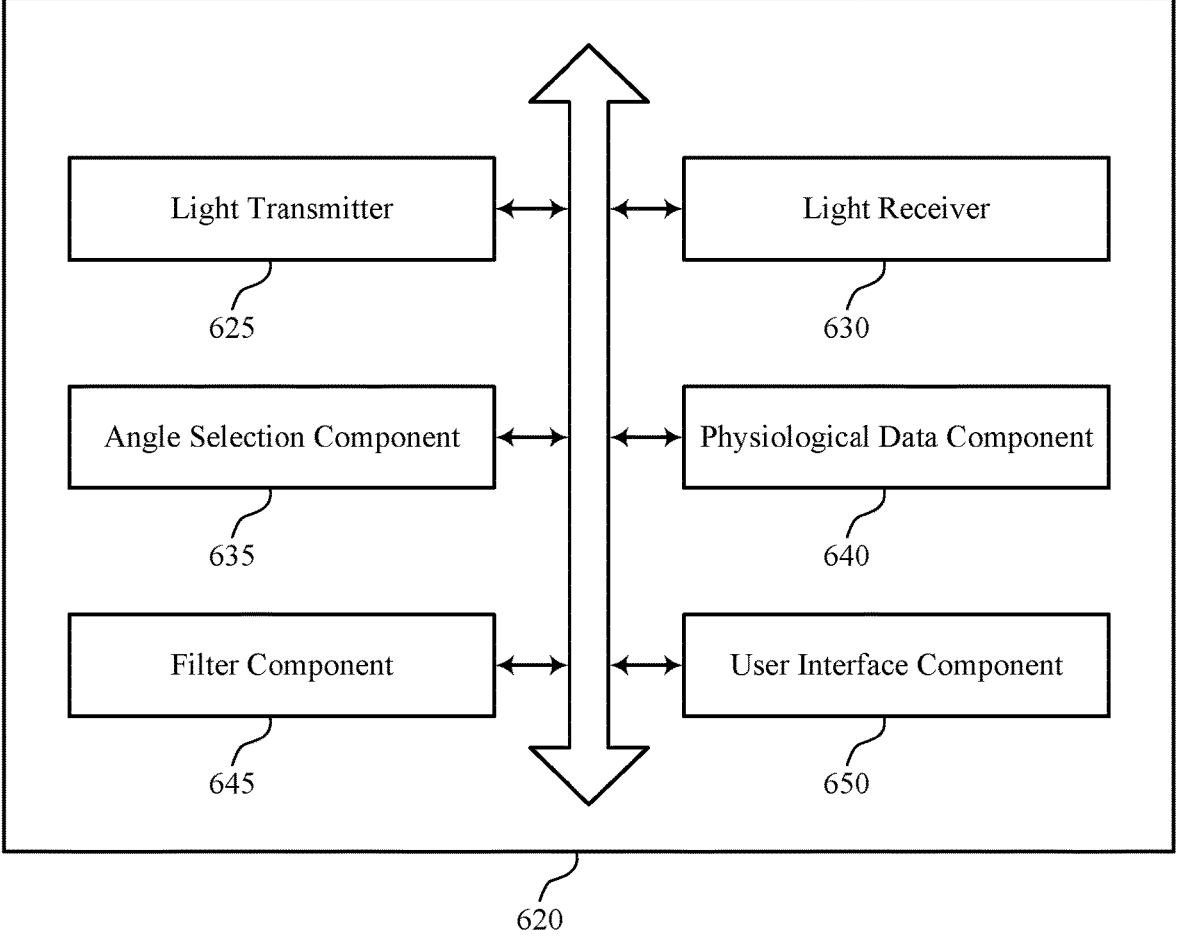
FIG. 6 illustrates a block diagram of a wearable device manager that supports techniques for measurement path multiplexing for a wearable device in accordance with aspects of the present disclosure.

FIG. 6 illustrates a block diagram 600 of a wearable device manager 620 that supports techniques for measurement path multiplexing for a wearable device in accordance with aspects of the present disclosure. The wearable device manager 620 may be an example of aspects of a wearable device manager or a wearable device manager 520, or both, as described herein. The wearable device manager 620, or various components thereof, may be an example of means for performing various aspects of techniques for measurement path multiplexing for a wearable device as described herein. For example, the wearable device manager 620 may include a light transmitter 625, a light receiver 630, an angle selection component 635, a physiological data component 640, a filter component 645, a user interface component 650, or any combination thereof. Each of these components may communicate, directly or indirectly, with one another (e.g., via one or more buses).

The light transmitter 625 may be configured as or otherwise support a means for transmitting first light using a light-emitting component of a wearable device, wherein the first light is associated with a first wavelength, and wherein the first light is transmitted into a tissue of a user via a plurality of transmission angles. The light receiver 630 may be configured as or otherwise support a means for receiving the first light using a photodetector of the wearable device, wherein the first light is received from the tissue of the user via a plurality of reception angles. The angle selection component 635 may be configured as or otherwise support a means for selecting a transmission angle from the plurality of transmission angles and a reception angle from the plurality of reception angles based at least in part on a comparison of a plurality of signal quality metrics associated with the plurality of transmission angles and the plurality of reception angles. The physiological data component 640 may be configured as or otherwise support a means for acquiring physiological data associated with the user based at least in part on additional light transmitted by the light-emitting component via the transmission angle and received by the photodetector via the reception angle, wherein the additional light is associated with the first wavelength.

In some examples, the angle selection component 635 may be configured as or otherwise support a means for determining a plurality of power consumption metrics associated with the plurality of transmission angles and the plurality of reception angles, wherein selecting the transmission angle and the reception angle is based at least in part on a comparison of the plurality of power consumption metrics.

In some examples, the light-emitting component is disposed within a surface of the wearable device at a first position. In some examples, the photodetector is disposed within the surface of the wearable device at a second position that is a distance away from the first position in a first direction relative to the surface. In some examples, the transmission angle is directed at least partially along a second direction relative to the surface that is opposite the first direction.

In some examples, the photodetector is disposed within a surface of the wearable device at a first position. In some examples, the light-emitting component is disposed within the surface of the wearable device at a second position that is a distance away from the first position in a first direction relative to the surface. In some examples, the reception angle is directed at least partially along a second direction relative to the surface that is opposite the first direction.

In some examples, the filter component 645 may be configured as or otherwise support a means for selectively adjusting one or more parameters of a first angular filter component associated with the light-emitting component, wherein transmitting the first light via the plurality of transmission angles is based at least in part on selectively adjusting the one or more parameters of the first angular filter component.

In some examples, the filter component 645 may be configured as or otherwise support a means for selectively adjusting one or more additional parameters of a second angular filter component associated with the photodetector, wherein receiving the first light via the plurality of reception angles is based at least in part on selectively adjusting the one or more additional parameters of the second angular filter component.

In some examples, the first angular filter component, the second angular filter component, or both, comprise a switchable angular filter, a prismatic structure, a micro-optical structure, a pixelated structure, or any combination thereof.

In some examples, the light-emitting component comprises a laser, and the light transmitter 625 may be configured as or otherwise support a means for scanning through the plurality of transmission angles using the laser, wherein transmitting the first light via the plurality of transmission angles is based at least in part on scanning through the plurality of transmission angles using the laser.

In some examples, the light transmitter 625 may be configured as or otherwise support a means for transmitting second light using the light-emitting component of the wearable device, wherein the second light is associated with a second wavelength, and wherein the second light is transmitted into the tissue of the user via the plurality of transmission angles, an additional plurality of transmission angles, or both. In some examples, the light receiver 630 may be configured as or otherwise support a means for receiving the second light using the photodetector of the wearable device, wherein the second light is received from the tissue of the user via the plurality of reception angles, an additional plurality of reception angles, or both. In some examples, the angle selection component 635 may be configured as or otherwise support a means for selecting a second transmission angle from the plurality of transmission angles or the additional plurality of transmission angles, and selecting a second reception angle from the plurality of reception angles or the additional plurality of reception angles. In some examples, the physiological data component 640 may be configured as or otherwise support a means for acquiring the physiological data, additional physiological data, or both, based at least in part on additional light transmitted by the light-emitting component via the second transmission angle and received by the photodetector via the second reception angle.

In some examples, the transmission angle, and the angle selection component 635 may be configured as or otherwise support a means for selecting a second transmission angle from the plurality of transmission angles and a second reception angle from the plurality of reception angles, wherein the second transmission angle and the second reception angle are associated with the first wavelength and a second physiological parameter different from the first physiological parameter. In some examples, the transmission angle, and the physiological data component 640 may be configured as or otherwise support a means for acquiring additional physiological data associated with the second physiological parameter based at least in part on additional light transmitted by the light-emitting component via the second transmission angle and received by the photodetector via the second reception angle, wherein the additional light is associated with the first wavelength.

In some examples, the first physiological parameter comprises a blood oxygen saturation metric. In some examples, the second physiological parameter comprises a heart rate metric, a HRV metric, or both.

In some examples, the plurality of transmission angles and the plurality of reception angles are associated with a plurality of transmission-reception angle pairs, where each transmission-reception angle pair comprises a respective transmission angle from the plurality of transmission angles and a respective reception angle from the plurality of reception angles. In some examples, the plurality of transmission-reception angle pairs are associated with a plurality of penetration depths into the tissue of the user, a plurality of optical path lengths within the tissue of the user, or both.

In some examples, the additional light is associated with a first penetration depth, and the light transmitter 625 may be configured as or otherwise support a means for transmitting, using the light-emitting component, second light associated with a second wavelength different from the first wavelength, the second light associated with a second penetration depth, a second optical path length, or both. In some examples, the additional light is associated with a first penetration depth, and the light receiver 630 may be configured as or otherwise support a means for receiving the second light using the photodetector. In some examples, the additional light is associated with a first penetration depth, and the physiological data component 640 may be configured as or otherwise support a means for selectively modifying one or more parameters associated with the physiological data based at least in part on a signal generated in response to the second light received at the photodetector.

In some examples, the user interface component 650 may be configured as or otherwise support a means for causing a GUI of a user device to display information associated with the physiological data.

In some examples, the wearable device comprises a wearable ring device.

Figure 7:
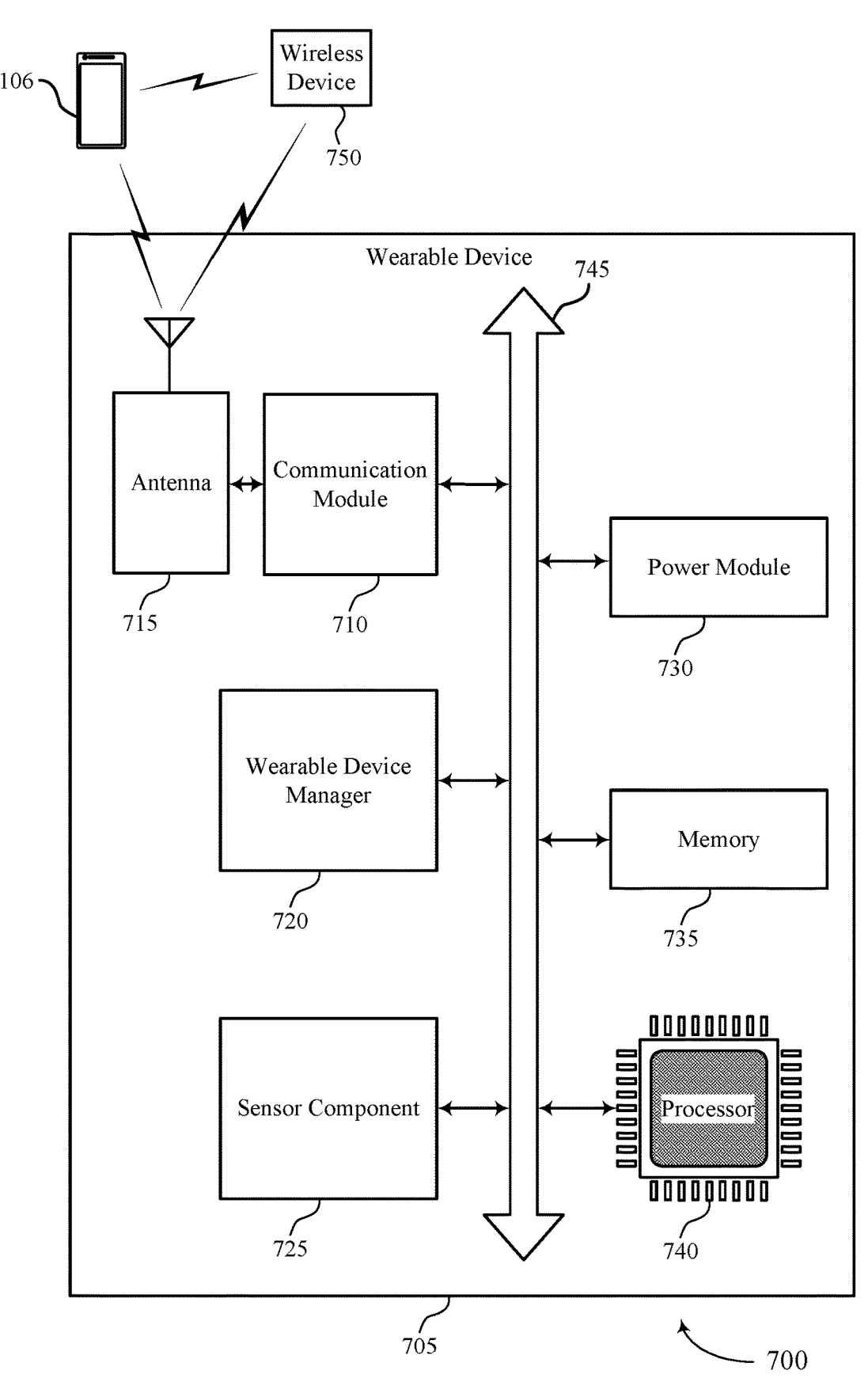
FIG. 7 illustrates a diagram of a system including a device that supports techniques for measurement path multiplexing for a wearable device in accordance with aspects of the present disclosure.

FIG. 7 illustrates a diagram of a system 700 including a device 705 that supports techniques for measurement path multiplexing for a wearable device in accordance with aspects of the present disclosure. The device 705 may be an example of or include the components of a device 505 as described herein. The device 705 may include an example of a wearable device 104, as described previously herein. The device 705 may include components for bi-directional communications including components for transmitting and receiving communications with a user device 106 and a server 110, such as a wearable device manager 720, a communication module 710, an antenna 715, a sensor component 725, a power module 730, a memory 735, a processor 740, and a wireless device 750. These components may be in electronic communication or otherwise coupled (e.g., operatively, communicatively, functionally, electronically, electrically) via one or more buses (e.g., a bus 745).

For example, the wearable device manager 720 may be configured as or otherwise support a means for transmitting first light using a light-emitting component of a wearable device, wherein the first light is associated with a first wavelength, and wherein the first light is transmitted into a tissue of a user via a plurality of transmission angles. The wearable device manager 720 may be configured as or otherwise support a means for receiving the first light using a photodetector of the wearable device, wherein the first light is received from the tissue of the user via a plurality of reception angles. The wearable device manager 720 may be configured as or otherwise support a means for selecting a transmission angle from the plurality of transmission angles and a reception angle from the plurality of reception angles based at least in part on a comparison of a plurality of signal quality metrics associated with the plurality of transmission angles and the plurality of reception angles. The wearable device manager 720 may be configured as or otherwise support a means for acquiring physiological data associated with the user based at least in part on additional light transmitted by the light-emitting component via the transmission angle and received by the photodetector via the reception angle, wherein the additional light is associated with the first wavelength.

By including or configuring the wearable device manager 720 in accordance with examples as described herein, the device 705 may support techniques for reduced power consumption and improved utilization of processing capability.

FIG. 8 illustrates a flowchart showing a method 800 that supports techniques for measurement path multiplexing for a wearable device in accordance with aspects of the present disclosure. The operations of the method 800 may be implemented by a wearable device or its components as described herein. For example, the operations of the method 800 may be performed by a wearable device as described with reference to FIGS. 1 through 7. In some examples, a wearable device may execute a set of instructions to control the functional elements of the wearable device to perform the described functions. Additionally, or alternatively, the wearable device may perform aspects of the described functions using special-purpose hardware.

At 805, the method may include transmitting first light using a light-emitting component of a wearable device, wherein the first light is associated with a first wavelength, and wherein the first light is transmitted into a tissue of a user via a plurality of transmission angles. The operations of 805 may be performed in accordance with examples as disclosed herein. In some examples, aspects of the operations of 805 may be performed by a light transmitter 625 as described with reference to FIG. 6.

At 810, the method may include receiving the first light using a photodetector of the wearable device, wherein the first light is received from the tissue of the user via a plurality of reception angles. The operations of 810 may be performed in accordance with examples as disclosed herein. In some examples, aspects of the operations of 810 may be performed by a light receiver 630 as described with reference to FIG. 6.

At 815, the method may include selecting a transmission angle from the plurality of transmission angles and a reception angle from the plurality of reception angles based at least in part on a comparison of a plurality of signal quality metrics associated with the plurality of transmission angles and the plurality of reception angles. The operations of 815 may be performed in accordance with examples as disclosed herein. In some examples, aspects of the operations of 815 may be performed by an angle selection component 635 as described with reference to FIG. 6.

At 820, the method may include acquiring physiological data associated with the user based at least in part on additional light transmitted by the light-emitting component via the transmission angle and received by the photodetector via the reception angle, wherein the additional light is associated with the first wavelength. The operations of 820 may be performed in accordance with examples as disclosed herein. In some examples, aspects of the operations of 820 may be performed by a physiological data component 640 as described with reference to FIG. 6.

FIG. 9 illustrates a flowchart showing a method 900 that supports techniques for measurement path multiplexing for a wearable device in accordance with aspects of the present disclosure. The operations of the method 900 may be implemented by a wearable device or its components as described herein. For example, the operations of the method 900 may be performed by a wearable device as described with reference to FIGS. 1 through 7. In some examples, a wearable device may execute a set of instructions to control the functional elements of the wearable device to perform the described functions. Additionally, or alternatively, the wearable device may perform aspects of the described functions using special-purpose hardware.

At 905, the method may include transmitting first light using a light-emitting component of a wearable device, wherein the first light is associated with a first wavelength, and wherein the first light is transmitted into a tissue of a user via a plurality of transmission angles. The operations of 905 may be performed in accordance with examples as disclosed herein. In some examples, aspects of the operations of 905 may be performed by a light transmitter 625 as described with reference to FIG. 6.

At 910, the method may include receiving the first light using a photodetector of the wearable device, wherein the first light is received from the tissue of the user via a plurality of reception angles. The operations of 910 may be performed in accordance with examples as disclosed herein. In some examples, aspects of the operations of 910 may be performed by a light receiver 630 as described with reference to FIG. 6.

At 915, the method may include determining a plurality of power consumption metrics associated with the plurality of transmission angles and the plurality of reception angles. The operations of 915 may be performed in accordance with examples as disclosed herein. In some examples, aspects of the operations of 915 may be performed by an angle selection component 635 as described with reference to FIG. 6.

At 920, the method may include selecting a transmission angle from the plurality of transmission angles and a reception angle from the plurality of reception angles based at least in part on a comparison of a plurality of signal quality metrics associated with the plurality of transmission angles and the plurality of reception angles and a comparison of the plurality of power consumption metrics. The operations of 920 may be performed in accordance with examples as disclosed herein. In some examples, aspects of the operations of 920 may be performed by an angle selection component 635 as described with reference to FIG. 6.

At 925, the method may include acquiring physiological data associated with the user based at least in part on additional light transmitted by the light-emitting component via the transmission angle and received by the photodetector via the reception angle, wherein the additional light is associated with the first wavelength. The operations of 925 may be performed in accordance with examples as disclosed herein. In some examples, aspects of the operations of 925 may be performed by a physiological data component 640 as described with reference to FIG. 6.

It should be noted that the methods described above describe possible implementations, and that the operations and the steps may be rearranged or otherwise modified and that other implementations are possible. Furthermore, aspects from two or more of the methods may be combined.

A method is described. The method may include transmitting first light using a light-emitting component of a wearable device, wherein the first light is associated with a first wavelength, and wherein the first light is transmitted into a tissue of a user via a plurality of transmission angles, receiving the first light using a photodetector of the wearable device, wherein the first light is received from the tissue of the user via a plurality of reception angles, selecting a transmission angle from the plurality of transmission angles and a reception angle from the plurality of reception angles based at least in part on a comparison of a plurality of signal quality metrics associated with the plurality of transmission angles and the plurality of reception angles, and acquiring physiological data associated with the user based at least in part on additional light transmitted by the light-emitting component via the transmission angle and received by the photodetector via the reception angle, wherein the additional light is associated with the first wavelength.

An apparatus is described. The apparatus may include a processor, memory coupled with the processor, and instructions stored in the memory. The instructions may be executable by the processor to cause the apparatus to transmit first light using a light-emitting component of a wearable device, wherein the first light is associated with a first wavelength, and wherein the first light is transmitted into a tissue of a user via a plurality of transmission angles, receive the first light using a photodetector of the wearable device, wherein the first light is received from the tissue of the user via a plurality of reception angles, select a transmission angle from the plurality of transmission angles and a reception angle from the plurality of reception angles based at least in part on a comparison of a plurality of signal quality metrics associated with the plurality of transmission angles and the plurality of reception angles, and acquire physiological data associated with the user based at least in part on additional light transmitted by the light-emitting component via the transmission angle and received by the photodetector via the reception angle, wherein the additional light is associated with the first wavelength.

Another apparatus is described. The apparatus may include means for transmitting first light using a light-emitting component of a wearable device, wherein the first light is associated with a first wavelength, and wherein the first light is transmitted into a tissue of a user via a plurality of transmission angles, means for receiving the first light using a photodetector of the wearable device, wherein the first light is received from the tissue of the user via a plurality of reception angles, means for selecting a transmission angle from the plurality of transmission angles and a reception angle from the plurality of reception angles based at least in part on a comparison of a plurality of signal quality metrics associated with the plurality of transmission angles and the plurality of reception angles, and means for acquiring physiological data associated with the user based at least in part on additional light transmitted by the light-emitting component via the transmission angle and received by the photodetector via the reception angle, wherein the additional light is associated with the first wavelength.

A non-transitory computer-readable medium storing code is described. The code may include instructions executable by a processor to transmit first light using a light-emitting component of a wearable device, wherein the first light is associated with a first wavelength, and wherein the first light is transmitted into a tissue of a user via a plurality of transmission angles, receive the first light using a photodetector of the wearable device, wherein the first light is received from the tissue of the user via a plurality of reception angles, select a transmission angle from the plurality of transmission angles and a reception angle from the plurality of reception angles based at least in part on a comparison of a plurality of signal quality metrics associated with the plurality of transmission angles and the plurality of reception angles, and acquire physiological data associated with the user based at least in part on additional light transmitted by the light-emitting component via the transmission angle and received by the photodetector via the reception angle, wherein the additional light is associated with the first wavelength.

Some examples of the method, apparatuses, and non-transitory computer-readable medium described herein may further include operations, features, means, or instructions for determining a plurality of power consumption metrics associated with the plurality of transmission angles and the plurality of reception angles, wherein selecting the transmission angle and the reception angle may be based at least in part on a comparison of the plurality of power consumption metrics.

In some examples of the method, apparatuses, and non-transitory computer-readable medium described herein, the light-emitting component may be disposed within a surface of the wearable device at a first position, the photodetector may be disposed within the surface of the wearable device at a second position that may be a distance away from the first position in a first direction relative to the surface, and the transmission angle may be directed at least partially along a second direction relative to the surface that may be opposite the first direction.

In some examples of the method, apparatuses, and non-transitory computer-readable medium described herein, the photodetector may be disposed within a surface of the wearable device at a first position, the light-emitting component may be disposed within the surface of the wearable device at a second position that may be a distance away from the first position in a first direction relative to the surface, and the reception angle may be directed at least partially along a second direction relative to the surface that may be opposite the first direction.

In some examples of the method, apparatuses, and non-transitory computer-readable medium described herein, selectively adjusting one or more parameters of a first angular filter component associated with the light-emitting component, wherein transmitting the first light via the plurality of transmission angles may be based at least in part on selectively adjusting the one or more parameters of the first angular filter component.

In some examples of the method, apparatuses, and non-transitory computer-readable medium described herein, selectively adjusting one or more additional parameters of a second angular filter component associated with the photodetector, wherein receiving the first light via the plurality of reception angles may be based at least in part on selectively adjusting the one or more additional parameters of the second angular filter component.

In some examples of the method, apparatuses, and non-transitory computer-readable medium described herein, the first angular filter component, the second angular filter component, or both, comprise a switchable angular filter, a prismatic structure, a micro-optical structure, a pixelated structure, or any combination thereof.

In some examples of the method, apparatuses, and non-transitory computer-readable medium described herein, the light-emitting component comprises a laser and the method, apparatuses, and non-transitory computer-readable medium may include further operations, features, means, or instructions for scanning through the plurality of transmission angles using the laser, wherein transmitting the first light via the plurality of transmission angles may be based at least in part on scanning through the plurality of transmission angles using the laser.

Some examples of the method, apparatuses, and non-transitory computer-readable medium described herein may further include operations, features, means, or instructions for transmitting second light using the light-emitting component of the wearable device, wherein the second light may be associated with a second wavelength, and wherein the second light may be transmitted into the tissue of the user via the plurality of transmission angles, an additional plurality of transmission angles, or both, receiving the second light using the photodetector of the wearable device, wherein the second light may be received from the tissue of the user via the plurality of reception angles, an additional plurality of reception angles, or both, selecting a second transmission angle from the plurality of transmission angles or the additional plurality of transmission angles, and selecting a second reception angle from the plurality of reception angles or the additional plurality of reception angles, and acquiring the physiological data, additional physiological data, or both, based at least in part on additional light transmitted by the light-emitting component via the second transmission angle and received by the photodetector via the second reception angle.

In some examples of the method, apparatuses, and non-transitory computer-readable medium described herein, the transmission angle and the method, apparatuses, and non-transitory computer-readable medium may include further operations, features, means, or instructions for selecting a second transmission angle from the plurality of transmission angles and a second reception angle from the plurality of reception angles, wherein the second transmission angle and the second reception angle may be associated with the first wavelength and a second physiological parameter different from the first physiological parameter and acquiring additional physiological data associated with the second physiological parameter based at least in part on additional light transmitted by the light-emitting component via the second transmission angle and received by the photodetector via the second reception angle, wherein the additional light may be associated with the first wavelength.

In some examples of the method, apparatuses, and non-transitory computer-readable medium described herein, the first physiological parameter comprises a blood oxygen saturation metric and the second physiological parameter comprises a heart rate metric, a HRV metric, or both.

In some examples of the method, apparatuses, and non-transitory computer-readable medium described herein, the plurality of transmission angles and the plurality of reception angles may be associated with a plurality of transmission-reception angle pairs, where each transmission-reception angle pair comprises a respective transmission angle from the plurality of transmission angles and a respective reception angle from the plurality of reception angles and the plurality of transmission-reception angle pairs may be associated with a plurality of penetration depths into the tissue of the user, a plurality of optical path lengths within the tissue of the user, or both.

In some examples of the method, apparatuses, and non-transitory computer-readable medium described herein, the additional light may be associated with a first penetration depth and the method, apparatuses, and non-transitory computer-readable medium may include further operations, features, means, or instructions for transmitting, using the light-emitting component, second light associated with a second wavelength different from the first wavelength, the second light associated with a second penetration depth, a second optical path length, or both, receiving the second light using the photodetector, and selectively modifying one or more parameters associated with the physiological data based at least in part on a signal generated in response to the second light received at the photodetector.

Some examples of the method, apparatuses, and non-transitory computer-readable medium described herein may further include operations, features, means, or instructions for causing a GUI of a user device to display information associated with the physiological data.

In some examples of the method, apparatuses, and non-transitory computer-readable medium described herein, the wearable device comprises a wearable ring device.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method comprising:
transmitting first light using a light-emitting component of a wearable device, wherein the first light is associated with a first wavelength, and wherein the first light is transmitted into a tissue of a user via a plurality of transmission angles;
receiving the first light using a photodetector of the wearable device, wherein the first light is received from the tissue of the user via a plurality of reception angles;
selecting a transmission angle from the plurality of transmission angles and a reception angle from the plurality of reception angles based at least in part on a comparison of a plurality of signal quality metrics associated with the plurality of transmission angles and the plurality of reception angles; and
acquiring physiological data associated with the user based at least in part on additional light transmitted by the light-emitting component via the transmission angle and received by the photodetector via the reception angle, wherein the additional light is associated with the first wavelength.

2. The method of claim 1, further comprising:
determining a plurality of power consumption metrics associated with the plurality of transmission angles and the plurality of reception angles, wherein selecting the transmission angle and the reception angle is based at least in part on a comparison of the plurality of power consumption metrics.

3. The method of claim 1, wherein the light-emitting component is disposed within a surface of the wearable device at a first position, and wherein the photodetector is disposed within the surface of the wearable device at a second position that is a distance away from the first position in a first direction relative to the surface, and wherein the transmission angle is directed at least partially along a second direction relative to the surface that is opposite the first direction.

4. The method of claim 1, wherein the photodetector is disposed within a surface of the wearable device at a first position, and wherein the light-emitting component is disposed within the surface of the wearable device at a second position that is a distance away from the first position in a first direction relative to the surface, and wherein the reception angle is directed at least partially along a second direction relative to the surface that is opposite the first direction.

5. The method of claim 1, further comprising:
selectively adjusting one or more parameters of a first angular filter component associated with the light-emitting component, wherein transmitting the first light via the plurality of transmission angles is based at least in part on selectively adjusting the one or more parameters of the first angular filter component.

6. The method of claim 5, further comprising:
selectively adjusting one or more additional parameters of a second angular filter component associated with the photodetector, wherein receiving the first light via the plurality of reception angles is based at least in part on selectively adjusting the one or more additional parameters of the second angular filter component.

7. The method of claim 6, wherein the first angular filter component, the second angular filter component, or both, comprise a switchable angular filter, a prismatic structure, a micro-optical structure, a pixelated structure, or any combination thereof.

8. The method of claim 1, wherein the light-emitting component comprises a laser, the method further comprising:
scanning through the plurality of transmission angles using the laser, wherein transmitting the first light via the plurality of transmission angles is based at least in part on scanning through the plurality of transmission angles using the laser.

9. The method of claim 1, further comprising:
transmitting second light using the light-emitting component of the wearable device, wherein the second light is associated with a second wavelength, and wherein the second light is transmitted into the tissue of the user via the plurality of transmission angles, an additional plurality of transmission angles, or both;
receiving the second light using the photodetector of the wearable device, wherein the second light is received from the tissue of the user via the plurality of reception angles, an additional plurality of reception angles, or both;
selecting a second transmission angle from the plurality of transmission angles or the additional plurality of transmission angles, and selecting a second reception angle from the plurality of reception angles or the additional plurality of reception angles; and
acquiring the physiological data, additional physiological data, or both, based at least in part on additional light transmitted by the light-emitting component via the second transmission angle and received by the photodetector via the second reception angle.

10. The method of claim 1, wherein the transmission angle, the reception angle, and the physiological data are associated with a first physiological parameter, the method further comprising:
selecting a second transmission angle from the plurality of transmission angles and a second reception angle from the plurality of reception angles, wherein the second transmission angle and the second reception angle are associated with the first wavelength and a second physiological parameter different from the first physiological parameter; and
acquiring additional physiological data associated with the second physiological parameter based at least in part on additional light transmitted by the light-emitting component via the second transmission angle and received by the photodetector via the second reception angle, wherein the additional light is associated with the first wavelength.

11. The method of claim 10, wherein the first physiological parameter comprises a blood oxygen saturation metric, and wherein the second physiological parameter comprises a heart rate metric, a heart rate variability metric, or both.

12. The method of claim 1, wherein the plurality of transmission angles and the plurality of reception angles are associated with a plurality of transmission-reception angle pairs, where each transmission-reception angle pair comprises a respective transmission angle from the plurality of transmission angles and a respective reception angle from the plurality of reception angles, and wherein the plurality of transmission-reception angle pairs are associated with a plurality of penetration depths into the tissue of the user, a plurality of optical path lengths within the tissue of the user, or both.

13. The method of claim 1, wherein the additional light is associated with a first penetration depth, a first optical path length, or both, the method further comprising:

transmitting, using the light-emitting component, second light associated with a second wavelength different from the first wavelength, the second light associated with a second penetration depth, a second optical path length, or both;

receiving the second light using the photodetector; and selectively modifying one or more parameters associated with the physiological data based at least in part on a signal generated in response to the second light received at the photodetector.

14. The method of claim 1, wherein selecting the transmission angle and the reception angle comprises:

selecting the transmission angle from the plurality of transmission angles and the reception angle from the plurality of reception angles based at least in part on a comparison of a plurality of power consumption metrics associated with the plurality of transmission angles and the plurality of reception angles.

15. The method of claim 1, further comprising:

causing a graphical user interface of a user device to display information associated with the physiological data.

16. The method of claim 1, wherein the wearable device comprises a wearable ring device.

17. A wearable device, comprising:

a light-emitting component configured to generate light associated with one or more wavelengths;

a photodetector configured to receive the light emitted by the light-emitting component through a tissue of a user; and one or more processing components communicatively coupled with the light-emitting component and the photodetector, wherein the one or more processing components are configured to:

transmit, using the light-emitting component, first light associated with a first wavelength, wherein the first light is transmitted into the tissue of the user via a plurality of transmission angles;

receive the first light using the photodetector, wherein the first light is received from the tissue of the user via a plurality of reception angles;

select a transmission angle from the plurality of transmission angles and a reception angle from the plurality of reception angles based at least in part on a comparison of a plurality of signal quality metrics associated with the plurality of transmission angles and the plurality of reception angles; and acquire physiological data associated with the user based at least in part on additional light transmitted by the light-emitting component via the transmission angle and received by the photodetector via the reception angle, wherein the additional light is associated with the first wavelength.

18. The wearable device of claim 17, wherein the one or more processing components are further configured to:

determine a plurality of power consumption metrics associated with the plurality of transmission angles and the plurality of reception angles, wherein selecting the transmission angle and the reception angle is based at least in part on a comparison of the plurality of power consumption metrics.

19. The wearable device of claim 17, wherein the light-emitting component is disposed within a surface of the wearable device at a first position, and wherein the photodetector is disposed within the surface of the wearable device at a second position that is a distance away from the first position in a first direction relative to the surface, and wherein the transmission angle is directed at least partially along a second direction relative to the surface that is opposite the first direction.

20. The wearable device of claim 17, wherein the one or more processing components are further configured to:

selectively adjust one or more parameters of a first angular filter component associated with the light-emitting component, wherein transmitting the first light via the plurality of transmission angles is based at least in part on selectively adjusting the one or more parameters of the first angular filter component.

* * * * *